United States Patent [19]

Couch

[11] Patent Number: 5,782,821
[45] Date of Patent: Jul. 21, 1998

[54] BATTERY BOOT FOR A PORTABLE SURGICAL TOOL

[75] Inventor: Victor Alan Couch, Cumming, Ga.

[73] Assignee: Alan Couch, Cumming, Ga.

[21] Appl. No.: 856,845

[22] Filed: May 15, 1997

[51] Int. Cl.⁶ .......................... A61B 17/00; B65D 33/16
[52] U.S. Cl. ......................... 606/1; 383/71; 383/72; 383/74
[58] Field of Search ................ 383/71, 72, 74, 383/121; 150/161, 165; 606/1; 433/116

[56] References Cited

U.S. PATENT DOCUMENTS

| | | | |
|---|---|---|---|
| 3,507,282 | 4/1970 | Burding | 383/71 |
| 4,465,486 | 8/1984 | Hill | 383/71 |
| 4,561,540 | 12/1985 | Hunter et al. | 383/71 |
| 4,832,507 | 5/1989 | Herrington | 383/74 |
| 5,209,045 | 5/1993 | Howard, Jr. et al. | 383/72 |
| 5,480,302 | 1/1996 | Fife | 433/116 |

FOREIGN PATENT DOCUMENTS

| | | | |
|---|---|---|---|
| 221017 | 4/1962 | Austria | 383/71 |
| 79670 | 11/1962 | France | 383/71 |

Primary Examiner—Michael Powell Buiz
Assistant Examiner—Julian W. Woo

[57] ABSTRACT

A pre-sterilized battery boot functioning to cover a portable surgical tool battery of a portable surgical tool, the battery boot comprises a envelope, and at least one fastener circumferentially positioned around a top end of the envelope, the portable surgical tool battery is inserted within the envelope, the at least one fastener functions to functionally hold the envelope onto the portable surgical tool battery.

4 Claims, 4 Drawing Sheets

BATTERY BOOT FOR A PORTABLE SURGICAL TOOL

FIELD OF THE INVENTION

The present invention relates to medical devices. More particularly, the present invention relates to a sterile cover for a rechargeable battery.

BACKGROUND OF THE INVENTION

In an operating room, power tools are used in various procedures. Battery powered power tools are preferred. All devices used in the operating room must be sterilized in an autoclave at high temperatures. While many parts are engineered to with stand the elevated temperatures, batteries are not. The useful life of batteries is drastically reduced when subjected to autoclave temperatures, what is needed is a way of providing sterilized batteries without exposing them to high temperatures.

An extensive prior art search conducted in the appropriate class and subclass resulted in no prior art discovery.

SUMMARY OF THE MENTION

Chemical sterilization of equipment is inadequate for operating room conditions. Batteries, when subjected to the standard sterilization procedures of autoclaving, are elevated to temperatures which reduce the life of the battery significantly. An alternative to sterilization of the batteries is to place them in a sterilized container or wrapping. What is needed is a baglike container that is inexpensive, easy to install and encompasses the battery when attached to a sterilized power tool.

The present invention solved a long felt need for a device that permits the use of non-sterile batteries in an operating room environment.

Accordingly, it is an object of the present invention to decrease exposure of the batteries to high temperature autoclaving, thereby prolonging the useful life of the battery.

More particularly, it is an object of the present invention to provide a boot which surrounds a non-sterile battery.

In keeping with these objects, and with others which will become apparent hereinafter, one feature of the present invention resides, briefly stated, in sterile enclosure having three closed sides and an open top.

In accordance with another feature of the present invention, the open top is folded back on itself prior to inserting the battery so that a sterile environment is maintained.

Another feature of the present invention is that the closure device prevents the battery boot, for a portable surgical tool, from sliding off the battery and the portable powered tool.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

DESCRIPTION OF THE PREFERRED EMBODIMENT

Figure 1:
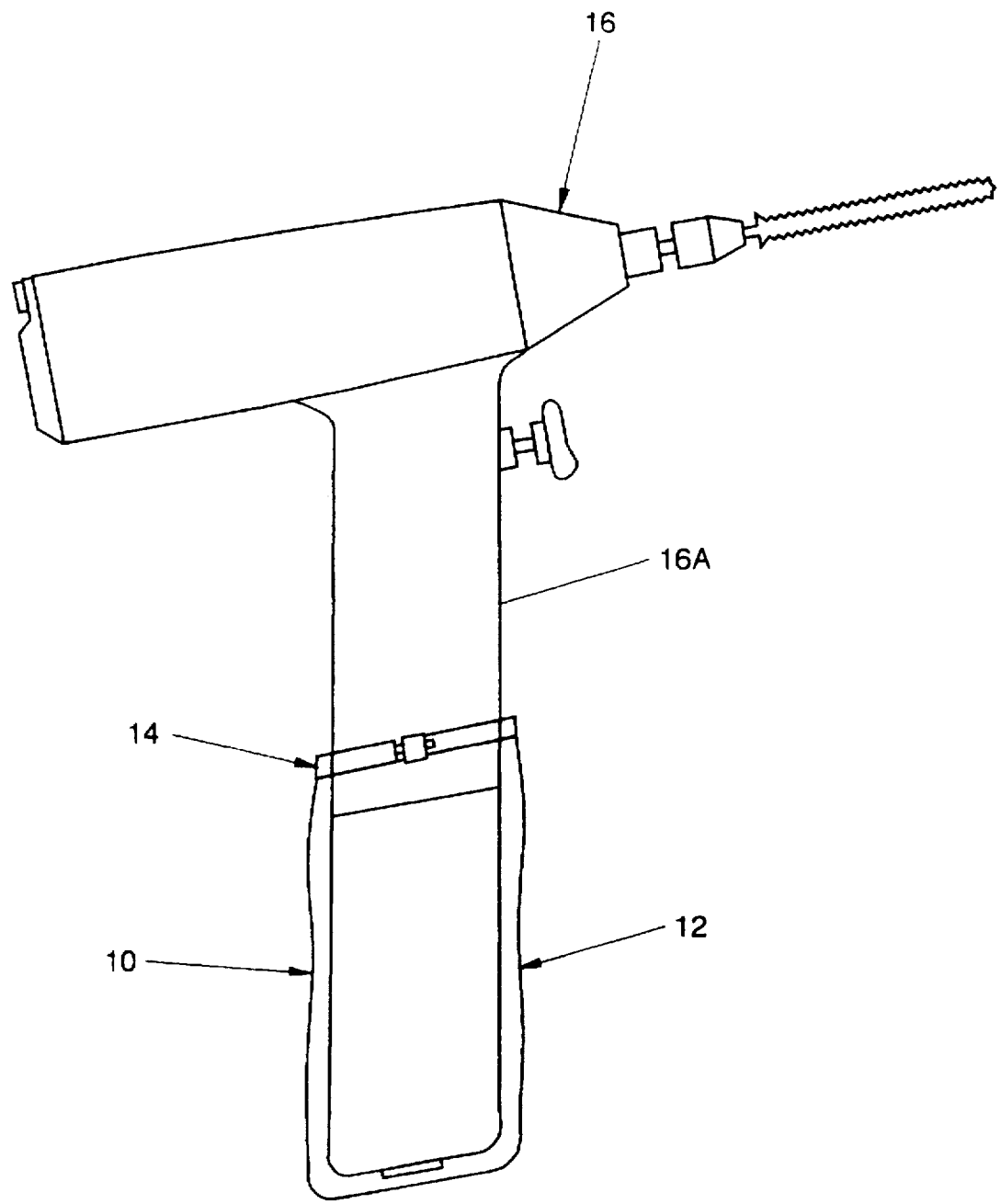
FIG. 1 is a right side view of a battery boot according to the present invention.

Firstly, referring to FIG. 1, there is shown a right side view of a pre-sterilized battery boot (10) functioning to cover a portable surgical tool battery (16A) of a portable surgical tool (16) according to this invention. The battery boot (10) comprises an envelope (12).

The pre-sterilized battery boot (10) comprises at least one fastener (14) circumferentially positioned around a top end of the envelope (12). The portable surgical tool battery (16A) is inserted within the envelope (12). The at least one fastener (14) functions to frictionally hold the envelope (12) onto the portable surgical tool battery (16A).

The at least one fastener (14) is selected from a group consisting of string, rubber band, and bungee. The at least one string fastener (14) further comprises a fastener synching means (14A) FIG. 2.

The envelope (12) is manufactured from a material selected from a group consisting of plastic, plastic composite, metal, metal alloy, fiberglass, rubber, rubber composite, epoxy, and carbon-graphite.

Figure 2:
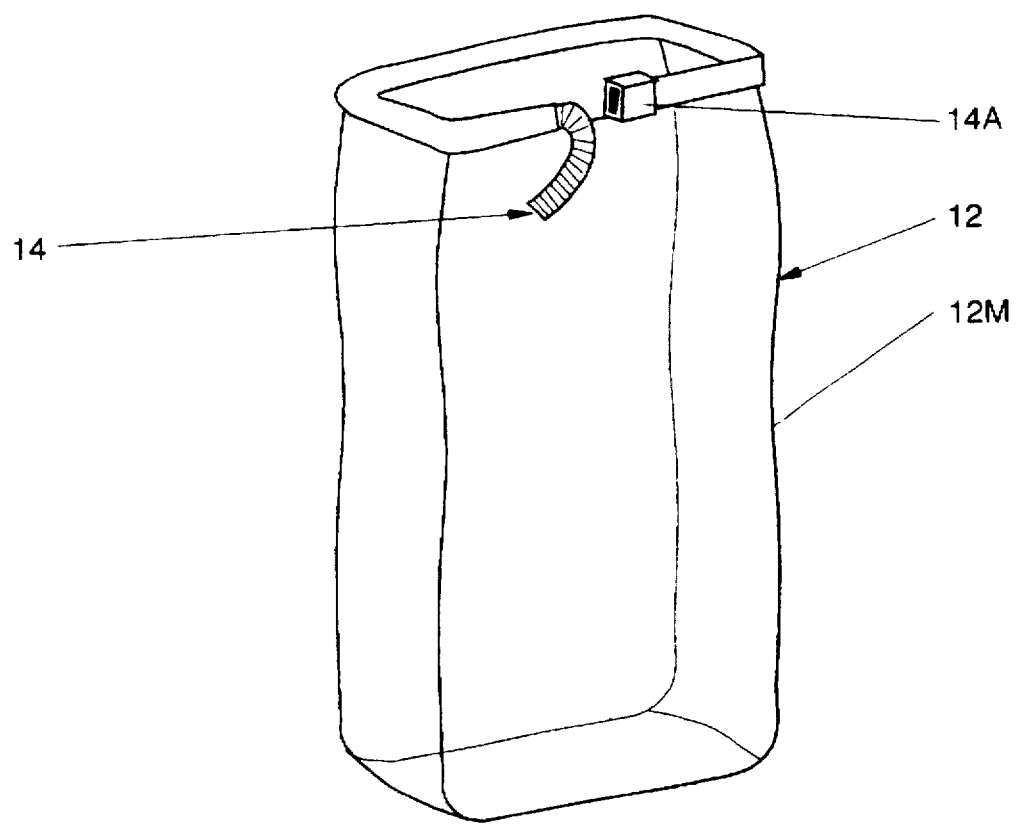
FIG. 2 is a perspective view of a battery boot according to the present invention.

Referring now to FIG. 2 there is shown a perspective view of a battery boot (10) which functions to cover a portable surgical tool battery (16A) of a portable surgical tool (16). The envelope (12) comprises an envelope middle (12M) forming an envelope compartment therein.

The at least one fastener (14) is selected from a group consisting of string, rubber band, and bungee. The at least one string fastener (14) further comprises a fastener synching means (14A).

Figure 3:
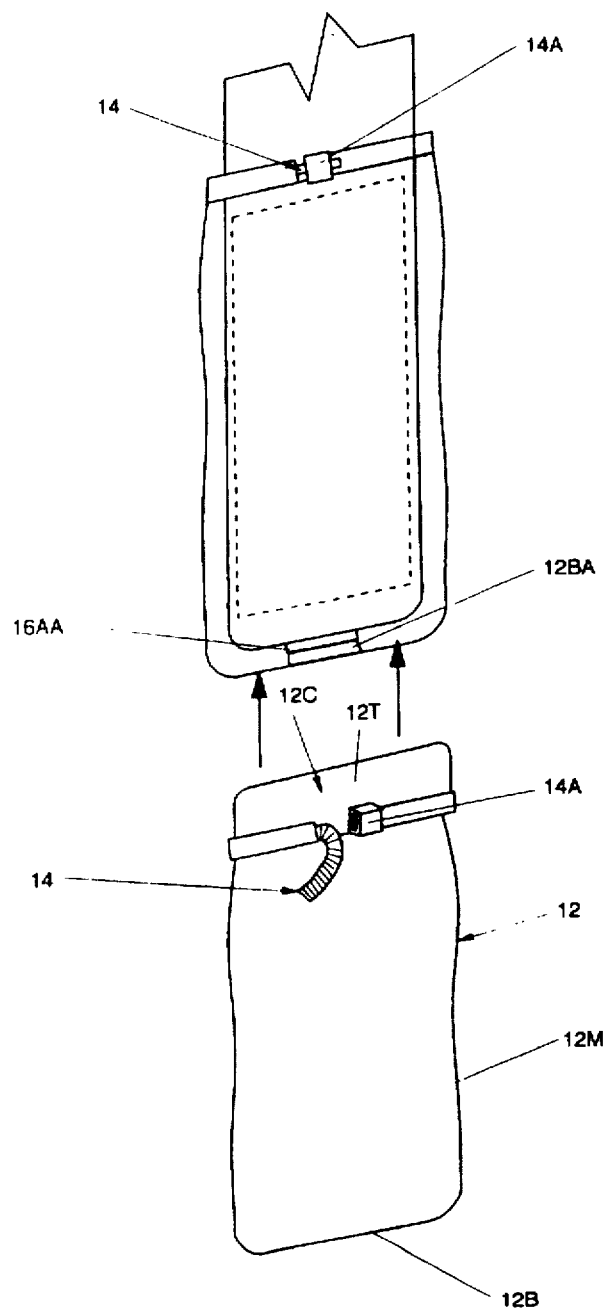
FIG. 3 is a perspective of a battery boot, having a closure means, inserted in accordance with this invention on to a battery.

Now, referring to FIG. 3 there is shown a perspective view of a pre-sterilized battery boot (10) which functions to cover a portable surgical tool battery. The pre-sterilized battery boot comprising an envelope (12) which comprises an envelope top (12T), an envelope bottom (12B), and an envelope middle (12M) forming an envelope compartment (12C) therein.

The envelope (12) comprises at least one fastener (14) circumferentially positioned around a top end of the envelope middle (12M). A portable surgical tool battery is inserted within the envelope compartment (12C). The at least one fastener (14) functions to frictionally hold the envelope (12) thereon.

The envelope bottom (12B) comprises at least one envelope bottom fastening means (12BA) which consist of hook or loop.

The at least one fastener (14) is selected from a group consisting of string, rubber band, and bungee.

The at least one string fastener (14) further comprises a fastener synching means (14A).

Figure 4:
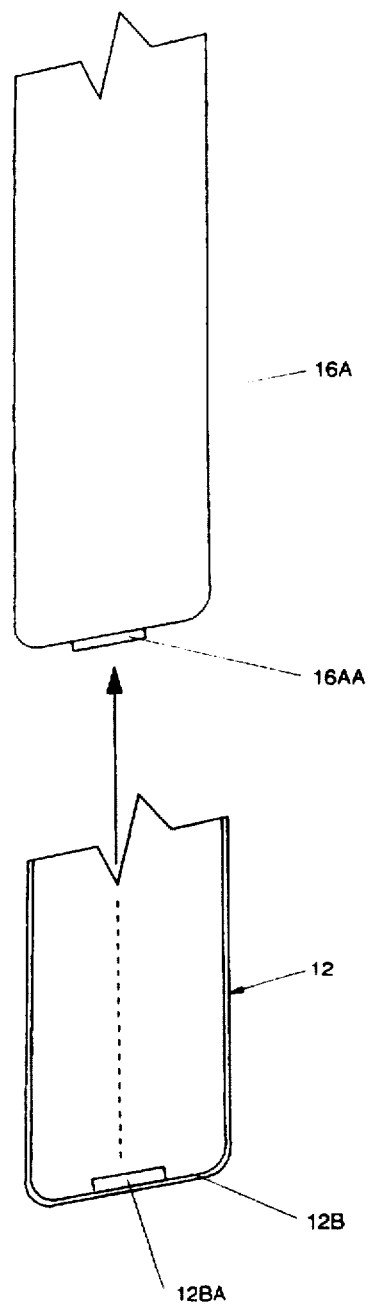
FIG. 4 is a perspective view of a battery boot with a alternative attachment means in accordance with this invention.

Lastly, referring to FIG. 4, which is a perspective view of a envelope (12), there is shown alternative attachment means. The portable surgical tool battery (16A) comprises at least one portable surgical tool battery fastening means (16AA) which consists of a complimentary configured loop or hook. The envelope bottom (12B) further comprises at least one envelope bottom fastening means (12BA) which consists of hook or loop and the portable surgical tool battery (16A), and further comprises at least one portable surgical tool battery fastening means (16AA) which consists of a complimentary configured loop or hook.

It will be understood that each of the elements described above, or two or more together, may also find a useful application in other types of constructions differing from the type described above.

While the invention has been illustrated and described as embodied in a Battery Boot for a Portable Surgical Tool, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims:

What is claimed Is:

1. A pre-steralized battery boot in combination with a portable surgical battery for a surgical tool, where said boot functions to cover said portable surgical tool battery, a) an envelope which comprises a top, a bottom, and a middle portion forming a envelope compartment for forming a tool battery therewithin; and b) at least one fastener circumferentially positioned around a top end of said middle portion, where the surgical tool battery is inserted within said envelope compartment, whereby said at least one fastener functions to frictionally hold said envelope about said portable surgical tool battery.

2. The battery boot is claimed in claim 1, wherein said bottom further comprises at least one fastening means which consist of hook or loop, and said portable surgical tool battery further includes atleast one fastening means which consist of a complimentary loop or hook.

3. The battery boot is claimed in claim 1, wherein the atleast one fastener is selected from the group consisting of string, rubber band, and bungee.

4. The battery boot is claimed in claim 3, wherein the atleast one string fastener further comprises a synching means.

\* \* \* \* \*